United States Patent
Kuroki et al.

(10) Patent No.: US 11,959,899 B2
(45) Date of Patent: *Apr. 16, 2024

(54) METHOD FOR PREPARING ORIGINAL DATA OF ODOR IMAGE

(71) Applicant: AROMA BIT, INC., Tokyo (JP)

(72) Inventors: Shunichiro Kuroki, Tokyo (JP); Kenichi Hashizume, Tokyo (JP); Megumi Takahashi, Tokyo (JP)

(73) Assignee: AROMA BIT, INC., Tokyo (JP)

( * ) Notice: Subject to any disclaimer, the term of this patent is extended or adjusted under 35 U.S.C. 154(b) by 43 days.

This patent is subject to a terminal disclaimer.

(21) Appl. No.: 17/855,701

(22) Filed: Jun. 30, 2022

(65) Prior Publication Data

US 2022/0365051 A1    Nov. 17, 2022

Related U.S. Application Data

(63) Continuation of application No. 16/686,970, filed on Nov. 18, 2019, now Pat. No. 11,408,872, which is a
(Continued)

(51) Int. Cl.
*G01N 33/00* (2006.01)
*G01N 5/02* (2006.01)
*G01N 27/12* (2006.01)

(52) U.S. Cl.
CPC .......... *G01N 33/0031* (2013.01); *G01N 5/02* (2013.01); *G01N 27/12* (2013.01);
(Continued)

(58) Field of Classification Search
CPC .......... G01N 33/0034; G01N 33/0047; G01N 33/0075; G01N 29/022; G01N 29/036;
(Continued)

(56) References Cited

U.S. PATENT DOCUMENTS

| 5,571,401 A | 11/1996 | Lewis et al. |
| 2012/0024042 A1 | 2/2012 | Vass et al. |

FOREIGN PATENT DOCUMENTS

| JP | H01-244335 A | 9/1989 |
| JP | H05-187986 A | 7/1993 |

(Continued)

OTHER PUBLICATIONS

International Search Report dated Aug. 15, 2017.
(Continued)

*Primary Examiner* — Benjamin R Schmitt
(74) *Attorney, Agent, or Firm* — FRESH IP PLC; Clifford D. Hyra; Aubrey Y. Chen

(57) ABSTRACT

Disclosed is a 4-method for preparing original data of an odor image includes a measurement result acquiring step of acquiring each measurement result measured with respect to the odor substance included in the sample in each of a plurality of sensor elements of an odor sensor, and a data processing step of generating the original data for representing the odor of the sample in the image by processing each of the acquired measurement results. Each of the sensor elements has different detection properties with respect to the odor substance. In a case where each of the original data items is represented in a small image, the odor of the sample is represented in an odor image in a predetermined display mode in which small images are assembled, and each of the small images is varied in accordance with the magnitude of the value of each original data item.

16 Claims, 5 Drawing Sheets

Related U.S. Application Data continuation of application No. PCT/JP2017/018580, filed on May 17, 2017.

(52) U.S. Cl.
CPC ..... *G01N 33/0034* (2013.01); *G01N 33/0047* (2013.01); *G01N 33/0075* (2013.01); *G01N 2291/021* (2013.01); *G01N 2291/0256* (2013.01)

(58) Field of Classification Search
CPC ....... G01N 2291/014; G01N 2291/021; G01N 2291/0255; G01N 2291/0426; G01N 33/0031; G01N 5/02
See application file for complete search history.

(56) References Cited

FOREIGN PATENT DOCUMENTS

| | | |
|---|---|---|
| JP | 11-500821 A | 1/1999 |
| JP | 11-503231 A | 3/1999 |
| JP | 11-352087 A | 12/1999 |
| JP | 2004-184124 A | 7/2004 |
| JP | 2012-021849 A | 2/2012 |
| JP | 2013-124953 A | 6/2013 |

OTHER PUBLICATIONS

First Office Action, Chinese App. No. 201780090188.5, dated Dec. 23, 2021.
Communication Pursuant to Article 94(3) EPC in EP Application No. 17910133.2-1001, dated Apr. 7, 2022.
Notice of Reasons for Refusal for JP App. No. 2021-176838, dated Nov. 1, 2022.

| ELAPSE TIME [SECOND] | SENSOR ELEMENT | | | | | | | | |
|---|---|---|---|---|---|---|---|---|---|
| | 11-01 | 11-02 | 11-03 | 11-04 | 11-05 | 11-06 | 11-07 | ... | 11-35 |
| 0 | 0.0 | 0.0 | 0.0 | 0.0 | 0.0 | 0.0 | 0.0 | | 0.0 |
| 1 | -1.3 | -0.3 | -2.0 | -0.3 | -5.7 | 0.7 | 0.3 | | 1.5 |
| 2 | 1.0 | 3.3 | -0.3 | 0.0 | -1.7 | -0.3 | -0.7 | | 4.5 |
| 3 | 1.0 | 0.0 | 0.3 | -0.3 | -3.3 | 0.7 | 1.3 | | 1.5 |
| 4 | 2.3 | 1.0 | -0.3 | 1.0 | -1.7 | 2.3 | 0.3 | | 0.9 |
| 5 | 4.7 | 3.7 | -1.0 | 4.7 | 0.3 | 6.3 | 3.0 | | 9.0 |
| 6 | 3.3 | 1.0 | 0.7 | 6.3 | 2.0 | 1.3 | 2.3 | | -1.9 |
| 7 | 1.7 | -1.0 | 0.0 | 1.3 | 0.7 | -1.0 | -1.0 | | 3.3 |
| 8 | 2.3 | 0.0 | 0.0 | 0.3 | -3.7 | 0.0 | -1.7 | | -0.8 |
| 9 | 1.7 | -0.3 | -1.0 | 0.7 | -6.0 | 0.3 | -1.0 | | 10.5 |
| 10 | 0.0 | -0.3 | -1.3 | 0.7 | 0.3 | -0.7 | 0.3 | | -0.3 |
| 11 | 2.0 | 1.0 | -0.3 | 1.0 | -3.0 | 0.3 | -0.7 | | 3.9 |
| 12 | 2.7 | 1.3 | 0.3 | 1.0 | -2.7 | 2.7 | 0.0 | | 5.3 |
| 13 | 3.7 | 2.3 | 0.0 | 4.7 | 0.3 | 1.3 | 3.3 | | 0.5 |
| 14 | 9.3 | 10.7 | 3.0 | 8.3 | 6.3 | 9.0 | 1.3 | | -0.3 |
| 15 | 0.0 | 5.0 | 1.7 | 2.3 | -7.7 | 4.0 | 0.0 | | 1.9 |
| 16 | -11.0 | -11.7 | -7.3 | -7.3 | -10.0 | -11.0 | -2.3 | | 2.2 |
| 17 | -13.3 | -7.7 | -4.0 | -10.0 | -8.0 | -8.3 | 1.0 | | 0.3 |
| 18 | -11.3 | 4.0 | -3.3 | -8.0 | -5.3 | -2.0 | 3.0 | | 2.4 |
| 19 | -5.7 | -3.7 | -3.7 | -0.7 | -4.0 | -2.7 | 2.7 | | 2.9 |
| 20 | 3.0 | -2.3 | -4.3 | 6.3 | -4.0 | -9.7 | 0.7 | ... | -0.5 |
| 21 | -4.7 | -5.7 | 0.0 | -5.0 | -1.3 | -6.7 | -1.7 | | 2.3 |
| 22 | 1.3 | -3.0 | -2.7 | -1.3 | -6.7 | -6.3 | -2.3 | | -3.5 |
| 23 | 0.3 | -3.3 | -1.7 | 0.0 | -4.0 | -5.3 | -2.0 | | 2.3 |
| 24 | -9.7 | -6.3 | -2.0 | -10.0 | -11.0 | -7.3 | -5.0 | | -0.9 |
| 25 | -5.3 | -8.7 | -2.7 | -9.7 | -10.7 | -7.3 | -6.0 | | 0.2 |
| 26 | -8.7 | -9.3 | -4.0 | -10.0 | -11.3 | -7.7 | -5.0 | | 3.2 |
| 27 | -7.0 | -8.7 | -2.3 | -8.3 | -10.7 | -7.7 | -5.0 | | 4.6 |
| 28 | -2.7 | -5.0 | -1.0 | -4.3 | -1.0 | -2.7 | -1.7 | | 2.4 |
| 29 | -1.3 | -4.7 | -2.3 | -4.0 | -9.7 | -4.3 | -1.7 | | 2.2 |
| 30 | -9.0 | -8.3 | -3.3 | -10.0 | -12.0 | -7.7 | -6.0 | | 1.0 |
| 31 | -8.7 | -6.0 | -1.7 | -7.3 | -6.3 | -4.3 | -4.0 | | 3.0 |
| 32 | 1.3 | -6.3 | 0.0 | 0.7 | -7.3 | -5.7 | -3.0 | | 2.4 |
| 33 | -8.7 | -8.0 | -2.7 | -10.3 | -8.0 | -5.3 | -6.7 | | 3.2 |
| 34 | -8.0 | -10.0 | -4.3 | -11.7 | -12.0 | -9.0 | -7.3 | | 2.3 |
| 35 | -5.0 | -8.3 | -3.3 | -6.7 | -12.3 | -8.0 | -6.0 | | 1.5 |
| 36 | -7.3 | -5.7 | -2.3 | -6.7 | -9.3 | -3.7 | -4.3 | | 1.6 |
| 37 | -3.7 | -6.7 | -2.0 | -4.3 | -6.3 | -5.0 | -5.0 | | 0.4 |
| 38 | -6.0 | -6.7 | -2.0 | -5.7 | -3.0 | -4.7 | -4.7 | | -1.1 |
| 39 | -5.3 | -6.0 | -2.0 | -3.7 | -8.3 | -3.7 | -3.0 | | -0.6 |
| 40 | -10.7 | -4.7 | -2.7 | -7.3 | -6.7 | -2.7 | -4.0 | | 0.8 |

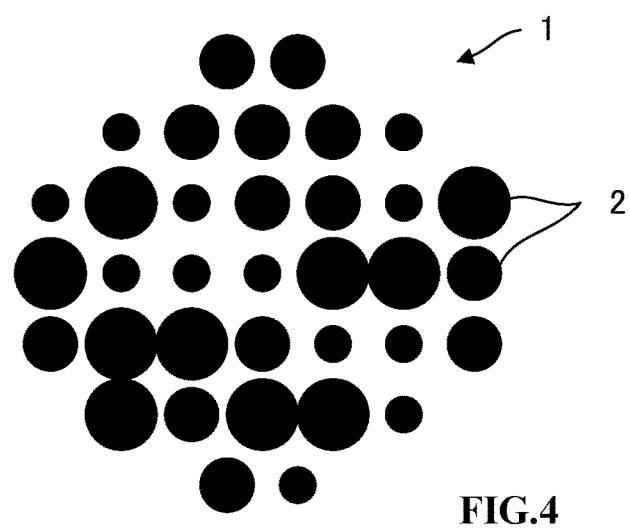
FIG.4
FIG.5
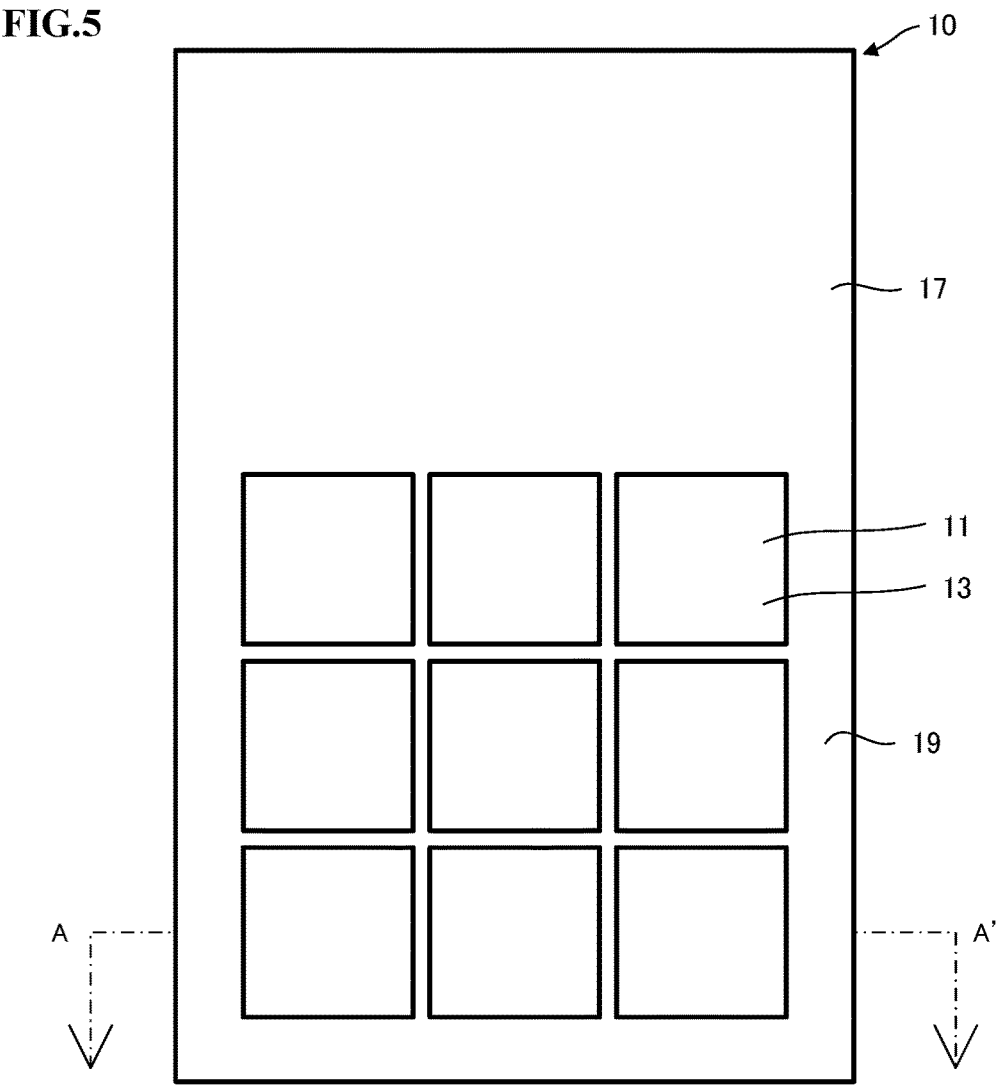

METHOD FOR PREPARING ORIGINAL DATA OF ODOR IMAGE

CROSS-REFERENCE TO RELATED APPLICATION

The present application is a continuation application of U.S. Nonprovisional application Ser. No. 16/686,970, filed Nov. 18, 2019, which is a continuation of International Application No. PCT/JP2017/018580, filed May 17, 2017. The contents of these applications are incorporated herein by reference in its entirety.

FIELD OF THE DISCLOSURE

The present invention relates to a method for preparing an original data of an odor image. Specifically, the present invention relates to a method for preparing an original data for representing an odor of a sample including an odor substance in an image.

BACKGROUND

In order to measure an odor of the air, a sensor including a quartz oscillator that specifically adsorbs an odor substance in the air is known (refer to Patent Document 1: JP 5-187986 A).

However, it is difficult to directly grasp what the odor is only by measuring the odor of the air with the sensor, and by storing a measurement result thereof.

The present disclosure has been made in consideration of the circumstances described above, and an exemplary object thereof is to provide a method for preparing an original data for representing an odor in an image such that a measurement result of the odor that is measured by using an odor sensor is easily visually grasped.

SUMMARY

In order to attain the object described above, the present disclosure is configured as follows.

(1) A method for preparing original data of an odor image in which the original data for representing an odor of a sample including an odor substance in an image is prepared, the method including: a measurement result acquiring step of acquiring each measurement result measured with respect to the odor substance included in the sample in each of a plurality of sensor elements included in an odor sensor, in a state in which each of the measurement results is associated with each of the plurality of sensor elements, by using the odor sensor; and a data processing step of generating the original data for representing the odor of the sample in the image by processing each of the acquired measurement results, the original data being associated with each of the plurality of sensor elements, wherein each of the plurality of sensor elements has different detection properties with respect to the odor substance, and in the data processing step, in a case where each of the original data items is represented in a small image corresponding to each of the sensor elements, the original data is generated such that the odor of the sample is represented in an image in a predetermined display mode in which a plurality of small images are assembled, and each of the small images is varied in accordance with a magnitude of a value of each original data item.

Further objects or other characteristics of the present invention will be apparent by preferred embodiments described below with reference to the attached drawings.

According to the present disclosure, it is possible to provide a method for preparing an original data for representing an odor in an image such that a measurement result of the odor that is measured by using an odor sensor is easily visually grasped.

BRIEF DESCRIPTION OF THE DRAWINGS

FIG. 1 is a measurement result database D1 which is acquired in a measurement result acquiring step of Embodiment 1;

FIG. 4 is an example of an image represented on the basis of original data which is generated in the data processing step S2 of Embodiment 1;

FIG. 5 is a plan view schematically illustrating an odor sensor 10 in Embodiment 1;

DETAILED DESCRIPTION

Embodiment 1

Figure 2:
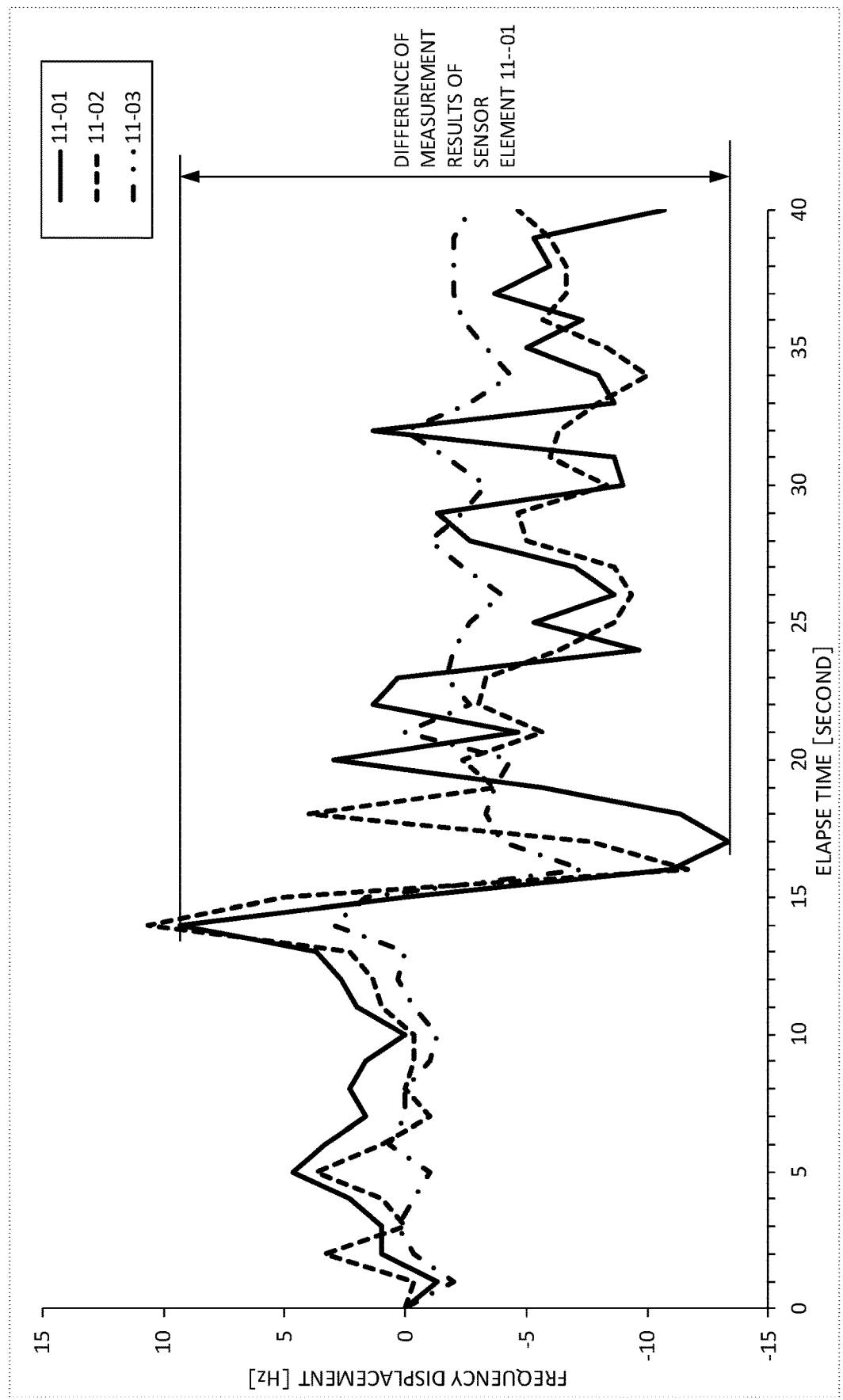
FIG. 2 is a graph showing the measurement result that is acquired in the measurement result acquiring step of Embodiment 1.

Hereinafter, a method for preparing an original data of an odor image according to Embodiment 1 will be described. The method for preparing an original data of an odor image according to Embodiment 1 is a method for preparing an original data for representing an odor of a sample including an odor substance in an image. The method for preparing an original data of an odor image according to Embodiment 1 includes a measurement result acquiring step and a data processing step.

In Embodiment 1, the "odor" can be acquired by a human or living things including the human as olfactory information and corresponds to a concept including a molecular simple substance or a group of molecules made of different molecules gathered with respective concentrations.

In Embodiment 1, the molecular simple substance or the group of molecules made of different molecules gathered with respective concentrations included in the odor is referred to as an "odor substance". However, in a broad sense, the odor substance may broadly mean a substance which can be adsorbed on a substance adsorbing membrane of an odor sensor 10, which will be described below. That is, since the "odor" contains a plurality of odor substances responsible for the odor in many cases, and a substance not recognized as the odor substance or an unknown odor substance may be present, a substance generally not regarded as an odor causing substance may be contained.

<Measurement Result Acquiring Step S1>

In a measurement result acquiring step S1, each measurement result measured with respect to an odor substance included in a sample by each of plurality of sensor elements 11 included in the odor sensor 10 is acquired by using the odor sensor 10. Each of the plurality of sensor elements 11 has different detection properties with respect to the odor substance. A specific configuration of the odor sensor 10 will be described below.

Each of the measurement results is acquired associated with each of the plurality of sensor elements 11. Specifically, the measurement result can be acquired as a measurement result database in which the measurement result is stored in a state where each of the sensor elements 11 and each of the measurement results measured in each of the sensor elements 11 are associated with each other.

FIG. 1 is a measurement result database D1 which is acquired in the measurement result acquiring step of Embodiment 1. In the measurement result database D1, the measurement result is stored in a state where each of the sensor elements 11 and each of the measurement results measured in each of the sensor elements 11 are associated with each other. In the measurement result database D1 illustrated in FIG. 1, the measurement result is stored in a state where the measurement results are respectively associated with a total of 35 sensor elements 11 of sensor elements 11-01 to 11-35. Incidentally, in FIG. 1, for the convenience of the description, the description of the sensor elements 11-08 to 11-34 is omitted.

Specifically, the measurement result is raw data which is detected by each of the sensor elements 11. In a case where the odor sensor 10, for example, is a quartz oscillator sensor (QCM), a temporal change in a resonance frequency of a quartz oscillator can be the raw data that is generated by the sensor element 11. That is, a resonance frequency at a plurality of time points having different elapse times from an operation start of the odor sensor 10 can be the measurement result according to the sensor element 11. For example, as illustrated in FIG. 1, as the measurement result measured in the sensor element 11-01, a resonance frequency measured after 14 seconds is "9.3", and a resonance frequency measured after 16 seconds is "−11.0", on the basis of a resonance frequency after 0 seconds from the operation start of the odor sensor 10. In addition, as the measurement result measured in the sensor element 11-02, a resonance frequency measured after 14 seconds from the operation start of the odor sensor 10 is "10.7", and a resonance frequency measured after 16 seconds from the operation start of the odor sensor 10 is "−11.7", on the basis of the resonance frequency after 0 seconds from the odor sensor 10. Incidentally, in the measurement, a time interval of recording the measurement result is not particularly limited and can be an interval of 1 second for example.

It is preferable that the measurement of the odor sensor 10 is performed a plurality of times, and an average value of the raw data items of the measurement that is performed a plurality of times is acquired as the measurement result. The number of times of the measurement is not particularly limited, and for example, can be three times. An average value according to an arithmetic average (an arithmetic means) can be adopted as the average value.

<Data Processing Step S2>

In a data processing step S2, the original data for representing the odor of the sample in an odor image 1 are generated by processing each of the measurement results acquired in the measurement result acquiring step S1, and the original data are associated with each of the plurality of sensor elements 11. In addition, in the data processing step S2, in a case where each of the original data items is represented in a small image 2 corresponding to each of the sensor elements 11, the original data is generated such that the odor of the sample is represented in the odor image 1 in a predetermined display mode in which a plurality of small images 2 are assembled, and each of the small images 2 is changed in accordance with the magnitude of the value of the original data.

The data processing step S2 includes each sub-step of a difference calculation sub-step S2-1, a logarithmic arithmetic sub-step S2-2, a value classifying sub-step S2-3, and an original data generating sub-step S2-4.

<Difference Calculation Sub-Step S2-1>

In the difference calculation sub-step S2-1, for each of the measurement result acquired in the measurement result acquiring step S1, a difference between a maximal value and a first minimal value after the maximal value (hereinafter, also referred to as a "minimal value immediately after the maximal value") is calculated. Then, in a case where there are a plurality of differences (between the maximal value and the minimal value immediately after the maximal value), the difference having the largest value is adopted as the difference of the measurement result. In such a manner, the difference associated with each of the plurality of sensor elements 11 is obtained for each of the measurement results.

FIG. 2 is a graph showing the measurement result that is acquired in the measurement result acquiring step of Embodiment 1. In FIG. 2, the vertical axis denotes a displacement amount [Hz] of a resonance frequency which is measured after a predetermined time, on the basis of the resonance frequency after 0 seconds from the operation start of the odor sensor 10, and the horizontal axis denotes an elapse time [second] from the operation start of the odor sensor 10. In FIG. 2, among the measurement results represented in the measurement result database D1, the measurement results of the sensor elements 11-01, 11-02, and 11-03 are illustrated. In FIG. 2, the measurement result of the sensor element 11-01 is represented by a solid line, the measurement result of the sensor element 11-02 is represented by a broken line, and the measurement result of the sensor element 11-03 is represented by a dashed-dotted line. It is obvious that graphs can also be prepared with respect to other sensor elements 11-04 to 11-35, similarly. In FIG. 2, in the sensor element 11-01, the difference of the measurement result is "22.6 Hz". That is, in the measurement result of the sensor element 11-01, the difference is the difference between the maximal value of "9.3 Hz" after an elapse time of 14 seconds from the operation start of the odor sensor 10, and a minimal value of "−13.3 Hz" after an elapse time of 17 seconds from the operation start of the odor sensor 10.

When the difference is calculated, the range of the elapse time from the operation start of the odor sensor 10 may be limited. For example, in a case where the measurement of the odor of the sample is started after 15 seconds from the operation start of the odor sensor 10, and the measurement of the odor of the sample is ended after 20 seconds from the operation start of the odor sensor 10, the range of the elapse time for calculating the difference can be set to an elapse time of 14 seconds to 25 seconds from the operation start of the odor sensor 10. Incidentally, the range of the elapse time can be arbitrarily set.

<Logarithmic Arithmetic Sub-Step S2-2>

In the logarithmic arithmetic sub-step S2-2, a logarithmic arithmetic operation is performed with respect to each of the differences calculated in the difference calculation sub-step S2-1, and thus, a logarithmic value associated with each of the plurality of sensor elements 11 is obtained. In the logarithmic arithmetic operation, the base is not particularly limited, and for example, can be 2. Incidentally, the difference is a difference between the maximal value and the minimal value and is a positive value (real number).

<Value Classifying Sub-Step S2-3>

In the value classifying sub-step S2-3, each of the logarithmic values obtained in the logarithmic arithmetic sub-step S2-2 is classified into ranges in accordance with the size of the value. The number of classified ranges is not particularly limited, and can be three ranges to five ranges, and the like, for example. Hereinafter, a case where the value is classified into three ranges will be described.

In the value classifying sub-step S2-3, first, among the plurality of logarithmic values of the respective samples which are obtained in the logarithmic arithmetic sub-step S2-2, a maximum logarithmic value and a minimum logarithmic value are identified. Next, a quotient in a case where a difference between the maximum logarithmic value and the minimum logarithmic value is divided by 3 is calculated. A numerical range between the maximum logarithmic value and the minimum logarithmic value can be partitioned into trisected ranges by using the quotient obtained as described above. That is, the numerical range can be trisected into a range from the minimum logarithmic value to a value in which the quotient is added to the minimum logarithmic value, a range from the value in which the quotient is added to the minimum logarithmic value to a value in which twice the quotient is added to the minimum logarithmic value, and a range from the value in which twice the quotient is added to the minimum logarithmic value to the maximum logarithmic value.

Next, each of the logarithmic values associated with each of the sensor elements 11 is classified into any range of three ranges. To each of the logarithmic values, a flag for identifying the classified range may be provided. For example, for the three trisected ranges, flags such as (1), (2), and (3) in an increasing order can be provided. Accordingly, the measurement result associated with each of the sensor elements 11 can be classified into three stages in accordance with the magnitude of the value.

Figure 3:
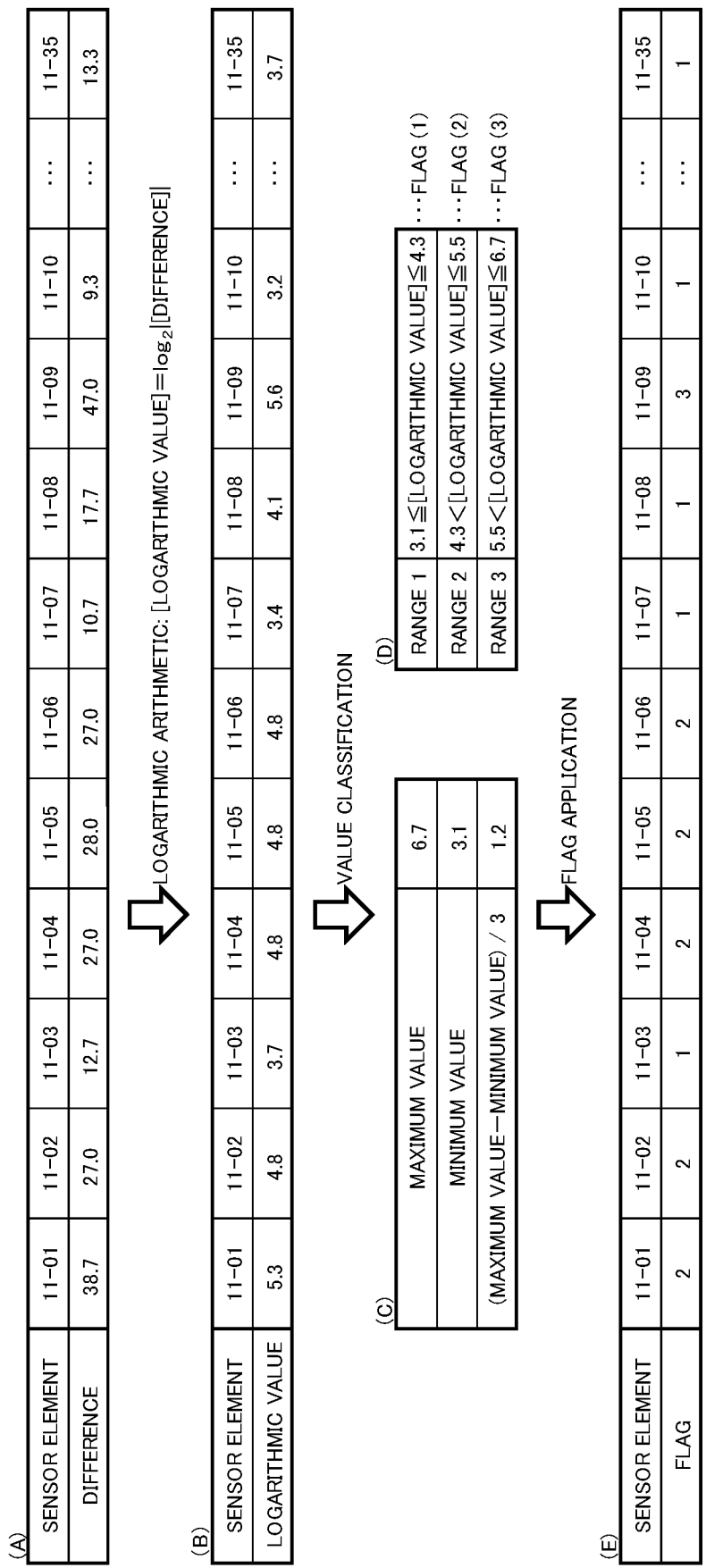
FIG. 3 is a diagram describing the outline of a data processing step S2 of Embodiment 1.

The data processing step S2 described above will be described in more detail by using FIG. 3. FIG. 3 is a diagram describing the outline of the data processing step S2 of Embodiment 1. In FIG. 3, Table (A) is a table showing the differences calculated with respect to a certain sample in the difference calculation sub-step S2-1. The value of each of the differences of each of the sensor elements 11-01 to 11-35 is shown. For example, in Table (A), the difference obtained in the sensor element 11-01 is "38.7", and the difference obtained in the sensor element 11-02 is "27.0". Incidentally, for the convenience of the description, indication of the values of the sensor elements 11-11 to 11-34 will be omitted (the same applies to Table (B) and Table (E) described below).

Next, according to the logarithmic arithmetic sub-step S2-2, the differences of each of the sensor elements 11 are subjected to logarithmic arithmetic processing. Here, the logarithmic arithmetic operation is represented by Formula (1) described below. That is, an absolute value of the value of the difference is subjected to logarithmic arithmetic operation by setting the base to 2, and thus, the logarithmic value is obtained.

[Logarithmic Value]=log2|[Difference]|   Formula (1)

Table (B) is a table showing the logarithmic values of each of the sensor elements 11 which are obtained in the logarithmic arithmetic sub-step S2-2. For example, in Table (B), the logarithmic value calculated based on the difference obtained in the sensor element 11-01 is "5.3", and the logarithmic value calculated based on the difference obtained in the sensor element 11-02 is "4.8".

Next, according to the value classifying sub-step S2-3, the logarithmic values of each of the sensor elements 11 are classified into three ranges on the basis of the obtained logarithmic value. Specifically, first, in the sample being measured, in the logarithmic values of the respective sensor elements 11, the maximum logarithmic value (maximum value) and the minimum logarithmic value (minimum value) are identified. Then, a quotient in a case where the difference between the maximum value and the minimum value is divided by 3 is calculated. The identified maximum value and minimum value, and the calculated quotient are shown in Table (C). In Table (C), the identified maximum value is "6.7", the identified minimum value is "3.1", and the calculated quotient is "1.2".

The logarithmic values of each of the sensor elements 11 are classified into three levels on the basis of the identified maximum value and minimum value, and the calculated quotient. The classification is performed on the basis of a classification rule as shown in Table (D). Specifically, the classification is performed on the basis of a classification rule in which a range of the smallest logarithmic values (range 1) is a range of 3.1≤[Logarithmic Value]≤4.3, a range of the second smallest logarithmic values (range 2) is a range of 4.3<[Logarithmic Value]≤5.5, and a range of the largest logarithmic values (range 3) is a range of 5.5<[Logarithmic Value]≤6.7.

Next, flags are applied to each of the sensor elements 11 on the basis of the classification result. The result of applying the flag to each of the sensor elements 11 is shown in Table (E). Flags (1) are applied to the sensor elements 11 in which the logarithmic value corresponding to range 1 is obtained, flags (2) are applied to the sensor elements 11 in which the logarithmic value corresponding to range 2 is obtained, and flags (3) are applied to the sensor elements 11 in which the logarithmic value corresponding to range 3 is obtained. For example, in Table (E), a flag (2) is applied to the sensor element 11-01, a flag (1) is applied to the sensor element 11-30, and a flag (3) is applied to the sensor element 11-09.

<Original Data Generating Sub-Step S2-4>

In the original data generating sub-step S2-4, the original data is generated based on the logarithmic value (measurement result) classified in the value classifying sub-step S2-3, the logarithmic value (measurement result) corresponding to each of the sensor elements 11. Each of the original data items has a value corresponding to each of the sensor elements 11.

The original data is a data which provide the basis of image data for representing the odor of the sample in an odor image 1. The original data is a data indicating the position or the size, the color, the shape, and the like of small images 2, but not a data (pixel data) indicating information of the color, the position, and the like of each pixel forming the odor image 1. The odor image 1 prepared on the basis of the original data includes a plurality of small images 2 represented by the original data items corresponding to each of the sensor elements 11. The odor image 1 can be represented in the predetermined display mode, as an assembly of the plurality of small images 2. Each of the small images 2 can be varied in accordance with the magnitude of the values of the corresponding original data. Specifically, the size, the color, and the shape of the small image 2 can be varied in accordance with the magnitude of the values of the corresponding original data. That is, in the original data generating sub-step S2-4, the original data is generated such that the odor of the sample is represented in the odor image 1 in the predetermined display mode. In addition, in the original data generating sub-step S2-4, the original data is generated such that each of the small images 2 is varied in accordance with the magnitude of the value of the original data.

FIG. 4 is an example of an image represented based on the original data which is generated in the data processing step S2 of Embodiment 1. The odor image 1 illustrated in FIG. 4 includes 35 small images 2, and each of the small images 2 is in the shape of a circle. Each of the small images 2 corresponds to each of the sensor elements 11-01 to 11-35, and is aligned in order from the upper left side. Specifically, in FIG. 4, two small images 2 in the first row from the upper side respectively correspond to the sensor elements 11-01 and 11-02 in order from the left side, and five small images 2 in the second row from the upper side respectively correspond to the sensor elements 11-03 to 11-07 in order from the left side. In addition, the small image 2 corresponding to the sensor element 11-03 (flag (1)) is represented by a small circle, the small image 2 corresponding to the sensor element 11-09 (flag (3)) is represented by a large circle, and the small image 2 corresponding to the sensor element 11-01 (flag (2)) is represented by a circle having a size between the small circle and the large circle.

In FIG. 4, the shape of all of the small images 2 is represented by a circle, but the shape of each of the small images 2 is not limited to a circle, and may be a square, a rectangle, a rhomboid, other indefinite shapes, and the like. In addition, it is not necessary that the shapes of all of the small images 2 are coincident with each other, and the small images 2 may respectively have different shapes. In FIG. 4, the color of each of the small images 2 is represented in black, but the color of each of the small images 2 is not limited to black, and may be represented by an arbitrary color. In addition, it is not necessary that the colors of all of the small images 2 are coincident with each other, and the small images 2 may be respectively represented by different colors.

In FIG. 4, each of the small images 2 is represented such that the size is different in accordance with the magnitude of the value of the corresponding original data. Specifically, the small image 2 is displayed large when the value of the original data increases, and the small image 2 is displayed small when the value of the original data decreases. Here, the size of each of the small images 2 to be displayed may be classified into a plurality of levels in accordance with the level classified in the value classifying sub-step S2-3. That is, in the value classifying sub-step S2-3, in a case where the classification is performed into three levels of flags (1), (2), and (3), the size of the small image 2 can also be classified and displayed in three levels.

In the predetermined display mode, it is preferable that an interval between the small images 2 is constant (an equal interval). In addition, in the predetermined display mode, it is preferable that the position of each of the small images 2 (the center or the gravity center of each of the small images 2) is constant (not changed in accordance with the value of the original data). As described above, the position or the interval of each of the small images 2 is constant, and thus, in a case where the size or the shape of each of the small images 2 is changed in accordance with the size of the value of the original data, it is possible to easily visually grasp the changed small image 2 by comparing the odor images 1 before and after being changed with each other. Incidentally, the interval between the small images 2 is not limited to being constant (the equal interval), and the odor image 1 may be a combination of a plurality of small images 2 having different shapes.

<Odor Sensor 10>

Figure 6:
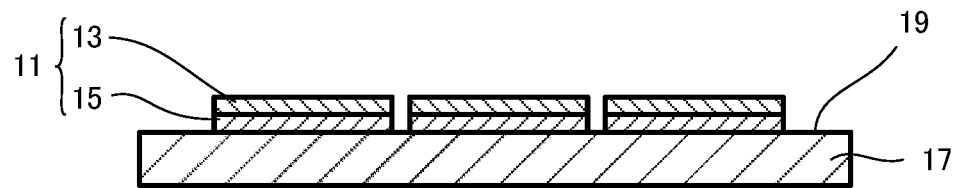
FIG. 6 is a sectional view schematically illustrating an A-A' sectional surface in FIG. 5.

FIG. 5 is a plan view schematically illustrating the odor sensor 10 in the first embodiment. FIG. 6 is a cross-sectional view schematically illustrating the A-A' cross section of FIG. 5. The odor sensor 10 includes a plurality of sensor elements 11. Each of the sensor elements 11 includes the substance adsorption membrane 13 that adsorbs the odor substance and a detector 15 that detects an adsorption state of the odor substance with respect to the substance adsorption membrane 13.

As illustrated in FIG. 6, the sensor element 11 includes the detector 15 and the substance adsorption membrane 13 provided on the surface of the detector 15. It is preferable that the substance adsorption membrane 13 covers the entire surface of the detector 15. That is, the size of the detector 15 is preferably the same as the formation range of the substance adsorption membrane 13, or smaller than the formation range of the substance adsorption membrane 13. Incidentally, a plurality of detectors 15 may be provided within the formation range of one substance adsorption membrane 13.

The plurality of sensor elements 11 is arranged on a sensor substrate 17 and aligned in a lattice pattern of three rows and three columns as illustrated in FIG. 4. In this instance, substance adsorption membranes 13 of adjacent sensor elements 11 are not in contact with each other or are insulated. It should be noted that the sensor elements 11 may not be aligned on the sensor substrate 17 and may be randomly arranged or aligned in a form other than three rows and three columns. Incidentally, in order to prepare the odor image 1 including 35 small images 2 as illustrated in FIG. 4, it is preferable to use 35 sensor elements 11 respectively corresponding to the small images 2. In such a case, it is not necessary that all of the sensor elements 11 are provided on one sensor substrate 17, and different sensor elements 11 may be provided on a plurality of sensor substrates 17.

In the plurality of sensor elements 11 arranged on the sensor substrate 17, properties of the respective substance adsorption membranes 13 are different from each other. Specifically, it is preferable that all the plurality of sensor elements 11 have the substance adsorption membranes 13 of different compositions, and that substance adsorption membranes 13 of the same property do not exist. Here, the property of the substance adsorption membrane 13 can be referred to as the adsorption characteristic of the odor substance with respect to the substance adsorption membrane 13. That is, one same odor substance (or an aggregate thereof) can exhibit different adsorption characteristics if the substance adsorption membrane 13 has different property. In FIG. 5 and FIG. 6, for the sake of convenience, all the substance adsorption membranes 13 are illustrated in the same manner. However, in practice, properties thereof are different from each other. Incidentally, it is not necessary that the adsorption properties of all of the substance adsorbing membranes 13 of each of the sensor elements 11 are different from each other, and among them, the sensor elements 11 provided with the substance adsorbing membranes 13 having the same adsorption properties may be provided.

As a material of the substance adsorption membrane 13, it is possible to use a thin film formed of a π electron conjugated polymer. This thin film can contain at least one of an inorganic acid, an organic acid, or an ionic liquid as a dopant. By changing the type or content of the dopant, it is possible to change the property of the substance adsorption membrane 13.

Examples of the π electron conjugated polymer preferably include, but are not limited to, a polymer having the π electron conjugated polymer as a skeleton such as polypyrrole and a derivative thereof, polyaniline and a derivative thereof, polythiophene and a derivative thereof, polyacetylene and a derivative thereof, or polyazulene and a derivative thereof.

In a case in which the π electron conjugated polymer is in an oxidized state and the skeleton polymer itself is a cation, conductivity can be developed by containing an anion as a dopant. Incidentally, in embodiments of the disclosure, a neutral π electron conjugated polymer not containing a dopant can be adopted as the substance adsorption membrane 13.

Specific examples of the dopant can include inorganic ions such as chlorine ion, chlorine oxide ion, bromine ion, sulfate ion, nitrate ion, and borate ion, organic acid anions such as alkylsulfonic acid, benzenesulfonic acid, and carboxylic acid, and polymer acid anions such as polyacrylic acid and polystyrene sulfonic acid.

In addition, it is possible to use a method of performing chemical equilibrium doping by allowing salt such as table salt or an ionic compound containing both a cation and an anion such as an ionic liquid to coexist with the neutral π electron conjugated polymer.

In a case in which a state in which one dopant unit (ion) enters per two repeating units included in the π electron conjugated polymer is set to 1, the content of the dopant in the π electron conjugated polymer may be adjusted in a range of 0.01 to 5, preferably in a range of 0.1 to 2. When the content of the dopant is set to be greater than or equal to the minimum value of this range, it is possible to inhibit disappearance of the characteristic of the substance adsorption membrane 13. In addition, when the content of the dopant is set to be less than or equal to the maximum value of this range, it is possible to inhibit a decrease in effect of the adsorption characteristic of the π electron conjugated polymer itself, which makes it difficult to produce the substance adsorption membrane 13 having a desirable adsorption characteristic. In addition, it is possible to inhibit a significant decrease in durability of the substance adsorption membrane 13 due to the dopant, which is a low molecular weight substance, when predominant in the membrane. Therefore, by setting the content of the dopant in the above-mentioned range, it is possible to suitably maintain detection sensitivity of the odor substance.

In the plurality of sensor elements 11, different types of π electron conjugated polymers can be used to vary the respective adsorption characteristics of the substance adsorption membranes 13. In addition, respective adsorption characteristics may be developed by changing the type or the content of the dopant while using the same kind of π electron conjugated polymer. For example, hydrophobic/hydrophilic properties of the substance adsorption membrane 13 can be changed by changing the type of the π electron conjugated polymer, the type and the content of the dopant, etc.

A thickness of the substance adsorption membrane 13 can be appropriately selected according to the characteristic of the odor substance to be adsorbed. For example, the thickness of the substance adsorption membrane 13 can be in a range of 10 nm to 10 μm, preferably 50 nm to 800 nm. When the thickness of the substance adsorption membrane 13 is less than 10 nm, sufficient sensitivity may not be obtained in some cases. In addition, when the thickness of the substance adsorption membrane 13 exceeds 10 lam, an upper limit of the weight detectable by the detector 15 may be exceeded.

The detector 15 has a function as a signal converter (transducer) which measures a change in physical, chemical, or electrical characteristic of the substance adsorption membrane 13 due to the odor substance adsorbed on the surface of the substance adsorption membrane 13 and outputs measurement data thereof as, for example, an electric signal. That is, the detector 15 detects an adsorption state of the odor substance on the surface of the substance adsorption membrane 13. Examples of the signal output as the measurement data by the detector 15 include physical information such as an electric signal, light emission, a change in electric resistance, or a change in vibration frequency.

The detector 15 is not particularly limited as long as the detector 15 is a sensor which measures the change in physical, chemical, or electrical characteristic of the substance adsorption membrane 13, and various sensors can be appropriately used. Specific examples of the detector 15 include a crystal oscillator sensor (QCM), a surface elastic wave sensor, a field effect transistor (FET) sensor, a charge coupled device sensor, an MOS field effect transistor sensor, a metal oxide semiconductor sensor, an organic conductive polymer sensor, an electrochemical sensor.

Incidentally, in the case of using the crystal oscillator sensor as the detector 15, although not illustrated, as an excitation electrode, electrodes may be provided on both sides of the crystal oscillator or a separated electrode may be provided on one side to detect a high Q value. In addition, the excitation electrode may be provided on the sensor substrate 17 side of the crystal oscillator with the sensor substrate 17 interposed therebetween. The excitation electrode can be formed of an arbitrary conductive material. Specific examples of the material of the excitation electrode include inorganic materials such as gold, silver, platinum, chromium, titanium, aluminum, nickel, nickel alloy, silicon, carbon, and carbon nanotube, and organic materials such as conductive polymers such as polypyrrole and polyaniline.

As illustrated in FIG. 6, the detector 15 can have a flat-plate shape. As illustrated in FIG. 5, a shape of the flat plate of the flat-plate shape can be quadrilateral or square. However, the shape can be of various shapes such as a circle or an ellipse. Further, the shape of the detector 15 is not limited to the flat plate shape. A thickness thereof may be altered, and a concave portion or a convex portion may be formed.

In a case in which the detector 15 uses an oscillator as the crystal oscillator sensor described above, it is possible to reduce the influence (crosstalk) received from another oscillator coexisting on the same sensor substrate 17 by changing resonance frequencies of respective oscillators in the plurality of sensor elements 11. It is possible to arbitrarily design the resonance frequencies so that the respective oscillators on the same sensor substrate 17 exhibit different sensitivities with respect to a certain frequency. The resonance frequency can be changed, for example, by adjusting the thickness of the oscillator or the substance adsorption membrane 13.

As the sensor substrate 17, it is possible to use a silicon substrate, a substrate made of quartz crystal, a printed wiring substrate, a ceramic substrate, a resin substrate, etc. In addition, the substrate is a multilayer wiring substrate such as an interposer substrate, and an excitation electrode for oscillating the quartz substrate, mounting wirings, and an electrode for energizing are disposed at arbitrary positions.

By adopting the configuration as described above, it is possible to obtain the odor sensor 10 including the plurality of sensor elements 11 having the substance adsorption membranes 13 whose adsorption characteristics of the odor substance are different from each other. As a result, in a case in which an odor of air containing a certain odor substance or a composition thereof is measured by the odor sensor 10, the odor substance or the composition thereof comes into contact with the substance adsorption membrane 13 of each sensor element 11 in the same manner. However, the odor substance is adsorbed to the respective substance adsorption membranes 13 in different modes. That is, an adsorption amount of the odor substance is different between the respective substance adsorption membranes 13. For this reason, a detection result of the detector 15 is different between the respective sensor elements 11. Therefore, pieces of measurement data by the detector 15 corresponding to the number of sensor elements 11 (substance adsorption membranes 13) included in the odor sensor 10 are generated for the certain odor substance or the composition thereof.

A set of measurement data (hereinafter referred to as odor data) generated by the odor sensor 10 by measuring the certain odor substance or the composition thereof is usually specific (unique) to a specific odor substance or a composition of the odor substance. For this reason, by measuring the odor data using the odor sensor 10, it is possible to identify the odor as an odor substance alone or as a composition (mixture) of odor substances.

Figure 7:
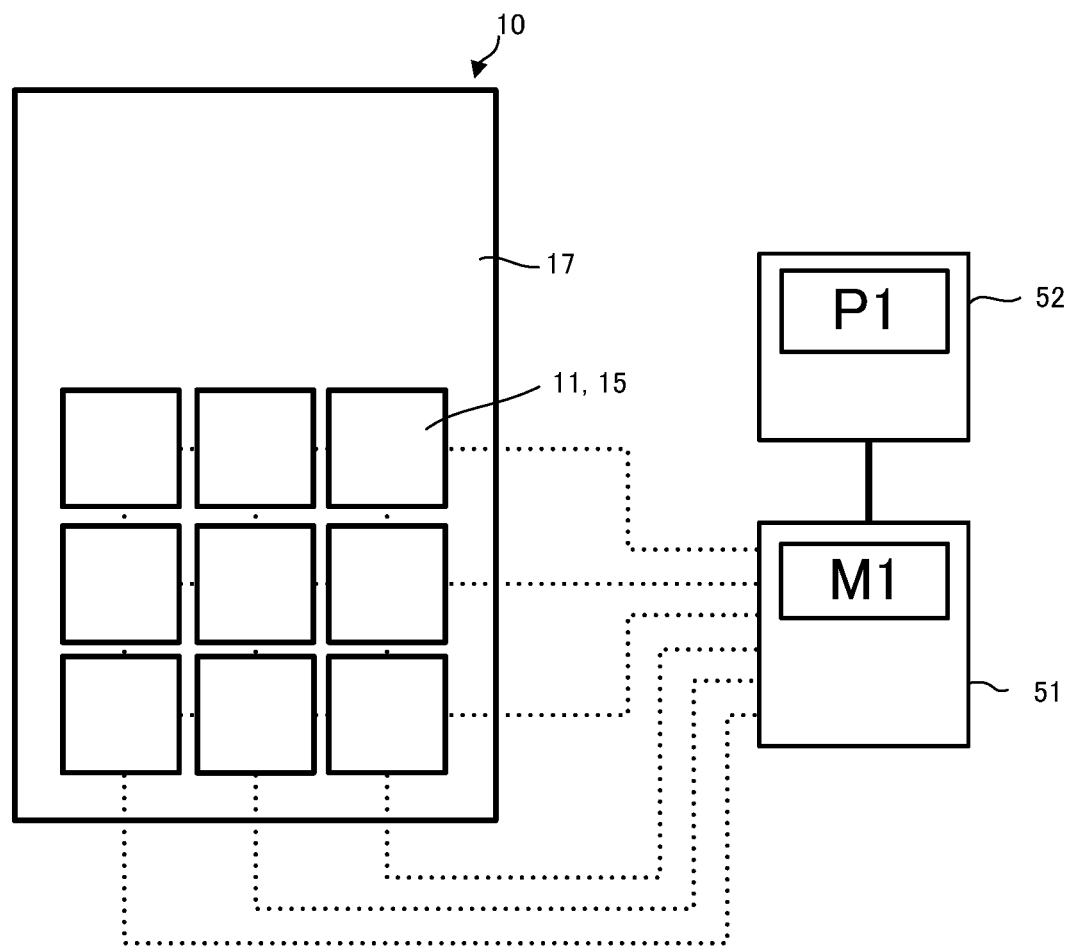
FIG. 7 is an explanatory diagram schematically illustrating an odor measurement mechanism of Embodiment 1.

Next, the configuration of an odor data acquiring means acquiring the odor data by using the odor sensor 10 will be described. FIG. 7 is an explanatory diagram schematically illustrating an odor measurement mechanism of Embodiment 1. The odor measurement, for example, can be performed by using an odor measurement apparatus. The odor measurement apparatus includes the odor sensor 10, an arithmetic processing device 51 connected to the odor sensor 10, and a storage device 52 connected to the arithmetic processing device 51. The measurement result measured by the odor sensor 10 can be processed in the arithmetic processing device 51, and can be stored in the storage device 52. An odor measurement means M1 realizing the measurement result acquiring step S1 is stored in the storage device 52 as a program P1, and the arithmetic processing device 51 execute the program, and thus, the odor sensor 10 can function as the odor measurement means. Incidentally, the acquisition of the odor data may be executed by other configurations without depending on the execution by the arithmetic processing device 51.

The odor measurement means (program) is capable of associating the measurement result obtained in each of the sensor elements 11 of the odor sensor 10 with each of the small images 2 of the odor image 1 one-to-one. At this time, there may be a correlative relationship between the arrangement of each of the sensor elements 11 on the odor sensor 10 and the arrangement of each of the small images 2 on the odor image 1, or there may be no correlative relationship (that is, random arrangement). For example, the small image 2 in which substance adsorption properties of the substance adsorbing membrane 13 provided in each of the sensor elements 11 are associated with the close sensor element 11 may be provided in a close position on the odor image 1. As described above, when there is a predetermined correlative relationship between the type of substance adsorbing membrane 13 of each of the sensor elements 11 and the arrangement of each of the small images 2, even in a case where a third party who does not know the information of the correlative relationship acquires the odor sensor 10, the third party is not possible to use the information of the correlative relationship. For this reason, such a third party is not capable of preparing the original data and the odor image 1 based on the correlative relationship.

Usage Example of Odor Image 1

The odor image obtained based on the original data prepared by the method for preparing original data of an odor image according to Embodiment 1 is capable of representing the odor of the sample in the odor image 1. That is, the odor image is capable of visually representing the odor of the sample. For example, it is possible to visually represent an odor of a food, a drink, the air (the atmosphere), and the like.

For example, when an odor image obtained based on an original data which is prepared by using a drink such as alcoholic liquor or coffee, and black tea as a sample is displayed on a package or a label of the drink, it is possible to visually obtain information of the odor with reference to the odor image, even in a case where the case of the drink is not opened. It is obvious that the sample is not limited to the drink, and any gas (atmosphere) containing the odor substance can be adopted as a sample without any particular limitation.

As described above, the method for preparing original data of an odor image according to Embodiment 1 has been described, but the present disclosure is not limited to Embodiment 1. For example, in the data processing step S2, the value classifying sub-step S2-3 is not the essential step, and thus, can be omitted. In this case, the odor image 1 may be changed in accordance with the magnitude of the value of the original data, without classifying the size, the color, and the shape of the small image 2 into the plurality of levels.

As described above, preferred embodiment of the present disclosure has been described, but the present disclosure is not limited thereto, and various modifications and changes can be performed within the scope of the point of the present disclosure. For example, the present disclosure includes the following points.

(Point 1) A method for preparing original data of an odor image in which the original data for representing an odor of a sample including an odor substance in an image is prepared, the method including: a measurement result acquiring step of acquiring each measurement result measured with respect to the odor substance included in the sample in each of a plurality of sensor elements included in an odor sensor, in a state in which each of the measurement results is associated with each of the plurality of sensor elements, by using the odor sensor; and a data processing step of generating the original data for representing the odor of the sample in the image by processing each of the acquired measurement results, the original data being associated with each of the plurality of sensor elements, wherein each of the plurality of sensor elements has different detection properties with respect to the odor substance, and in the data processing step, in a case where each of the original data items is represented in a small image corresponding to each of the sensor elements, the original data is generated such that the odor of the sample is represented in an image in a predetermined display mode in which a plurality of small images are assembled, and each of the small images is varied in accordance with a magnitude of a value of each original data item.

Accordingly, it is possible to represent the odor in the image such that the measurement result of the odor which is measured by using the odor sensor is easily visually grasped.

(Point 2) The predetermined display mode may be a display mode in which the plurality of small images respectively corresponding to the original data items are represented in a predetermined size, a predetermined color, and a predetermined shape with a predetermined interval.

(Point 3) In the data processing step, the original data may be classified into a plurality of levels in accordance with the value of the original data, and at least one of a size, a color, and a shape of the small image may be varied in accordance with each of the plurality of classified levels.

(Point 4) The plurality of sensor elements may respectively include a substance adsorbing membrane adsorbing the odor substance, and a detector detecting a state of adsorption of the odor substance with respect to the substance adsorbing membrane, and adsorption properties of the substance adsorbing membrane with respect to the odor substance may be different in each of the plurality of sensor elements.

(Point 5) A method for preparing an odor image represented based on the original data which is prepared by the method for preparing original data of an odor image according to any one of Point 1 to Point 4.

REFERENCE SIGNS LIST

1: odor image
2: small image
10: odor sensor
11: sensor element
13: substance adsorbing membrane
15: detector
17: sensor substrate
19: sensor surface
20: imaging device
21: lens portion
51: arithmetic processing device
52: storage device
D1: measurement result database

The invention claimed is:

1. A method for preparing original data of an odor image in which the original data for representing an odor of a sample including an odor substance in an image is prepared, the method comprising:
 a measurement result acquiring step of acquiring each measurement result measured with respect to the odor substance included in the sample in each of a plurality of sensor elements included in an odor sensor, in a state in which each of the measurement results is associated with each of the plurality of sensor elements, by using the odor sensor; and
 a data processing step of generating the original data for representing the odor of the sample in the image by processing each of the acquired measurement results, the original data being associated with each of the plurality of sensor elements,
 wherein the odor sensor is configured to output a change in physical, chemical, or electrical characteristics as the measurement result, the change being caused by a difference of adsorption amount of an odor substrate adsorbed on the plurality of sensor elements,
 wherein each of the plurality of sensor elements has different detection properties with respect to the odor substance,
 wherein the data processing step further comprises a difference calculation sub-step of calculating a difference between a first extremal value and a second extremal value after the first extremal value, and
 wherein, in the data processing step, in a case where each of the original data items is represented in a small image corresponding to each of the sensor elements, the original data is generated such that the odor of the sample is represented in an image in a predetermined display mode in which a plurality of small images are assembled, and each of the small images is varied in accordance with a magnitude of a value of each original data item.

2. The method for preparing original data of an odor image according to claim 1,
 wherein a difference having a largest value is adopted as the difference of the measurement result when there exists a plurality of the difference between the first extremal value and the second extremal value after the first extremal value in the difference calculation sub-step.

3. The method for preparing original data of an odor image according to claim 1,
 wherein the difference calculation sub-step is limitedly executed in a range of specific elapsed time from the start of measurement by the odor sensor.

4. The method for preparing original data of an odor image according to claim 1,
 wherein the predetermined display mode is a display mode in which the plurality of small images respectively corresponding to the original data items are represented in a predetermined size, a predetermined color, and a predetermined shape with a predetermined interval.

5. The method for preparing original data of an odor image according to claim 4,
 wherein, in the data processing step, (i) the original data is classified into a plurality of levels in accordance with the value of the original data, and (ii) at least one of a size, a color, and a shape of the small image is varied in accordance with each of the plurality of classified levels.

6. The method for preparing original data of an odor image according to claim 1,
 wherein the plurality of sensor elements respectively comprise:
 a substance adsorbing membrane adsorbing the odor substance,
 a detector detecting a state of adsorption of the odor substance with respect to the substance adsorbing membrane, and
 adsorption properties of the substance adsorbing membrane with respect to the odor substance are different in each of the plurality of sensor elements.

7. A method for preparing an odor image represented based on the original data which is prepared by the method for preparing original data of an odor image according to claim 1.

8. A method for preparing original data of an odor image in which the original data for representing an odor of a sample including an odor substance in an image is prepared, the method comprising:
 a measurement result acquiring step of acquiring each measurement result measured with respect to the odor substance included in the sample in each of a plurality of sensor elements included in an odor sensor, in a state in which each of the measurement results is associated with each of the plurality of sensor elements, by using the odor sensor; and
 a data processing step of generating the original data for representing the odor of the sample in the image by processing each of the acquired measurement results, the original data being associated with each of the plurality of sensor elements,
 wherein the odor sensor is configured to output a change in physical, chemical, or electrical characteristics as the measurement result, the change being caused by a difference of adsorption amount of an odor substrate adsorbed on the plurality of sensor elements, wherein each of the plurality of sensor elements has different detection properties with respect to the odor substance, wherein the data processing step further comprises a difference calculation sub-step of calculating a difference between a first extremal value and a second extremal value after the first extremal value, wherein the original data respectively corresponds to said calculated difference, and wherein, in the data processing step, in a case where each of the original data items is represented in a small image corresponding to each of the sensor elements, the original data is generated such that the odor of the sample is represented in an image in a predetermined display mode in which a plurality of small images are assembled, and each of the small images is varied in accordance with a magnitude of a value of each original data item.

9. The method for preparing original data of an odor image according to claim 8, wherein the original data respectively corresponds to a logarithmic value which a logarithmic arithmetic operation is performed with respect to the calculated difference, instead of corresponding to the calculated difference.

10. The method for preparing original data of an odor image according to claim 9, wherein the original data respectively corresponds to a number of classified ranges into which the logarithmic value is classified in accordance with its size, instead of corresponding to the logarithmic value.

11. The method for preparing original data of an odor image according to claim 8, wherein a difference having a largest value is adopted as the difference of the measurement result when there exists a plurality of the difference between the first extremal value and the second extremal value after the first extremal value in the difference calculation sub-step.

12. The method for preparing original data of an odor image according to claim 8, wherein the difference calculation sub-step is limitedly executed in a range of specific elapsed time from the start of measurement by the odor sensor.

13. The method for preparing original data of an odor image according to claim 8, wherein the predetermined display mode is a display mode in which the plurality of small images respectively corresponding to the original data items are represented in a predetermined size, a predetermined color, and a predetermined shape with a predetermined interval.

14. The method for preparing original data of an odor image according to claim 13, wherein, in the data processing step, (i) the original data is classified into a plurality of levels in accordance with the value of the original data, and (ii) at least one of a size, a color, and a shape of the small image is varied in accordance with each of the plurality of classified levels.

15. The method for preparing original data of an odor image according to claim 8, wherein the plurality of sensor elements respectively comprise:

a substance adsorbing membrane adsorbing the odor substance, a detector detecting a state of adsorption of the odor substance with respect to the substance adsorbing membrane, and adsorption properties of the substance adsorbing membrane with respect to the odor substance are different in each of the plurality of sensor elements.

16. A method for preparing an odor image represented based on the original data which is prepared by the method for preparing original data of an odor image according to claim 8.

* * * * *